US010139397B2

(12) United States Patent
Rao et al.

(10) Patent No.: US 10,139,397 B2
(45) Date of Patent: Nov. 27, 2018

(54) REACTION CUVETTE LOADING DEVICE AND CHEMILUMINESCENCE IMMUNOASSAY APPARATUS

(71) Applicant: Shenzhen New Industries Biomedical Engineering Co., LTD., Shenzhen, Guangdong (CN)

(72) Inventors: Wei Rao, Guangdong (CN); Dingping Ban, Guangdong (CN); Wanguan Yi, Guangdong (CN); Liang Zhu, Guangdong (CN); Yi Hu, Guangdong (CN); Xiaotao Chen, Guangdong (CN); Li Yin, Guangdong (CN); Wei Lin, Guangdong (CN)

(73) Assignee: SHENZHEN NEW INDUSTRIES BIOMEDICAL ENGINEERING CO., LTD., Shenzhen, Guangdong (CN)

( * ) Notice: Subject to any disclaimer, the term of this patent is extended or adjusted under 35 U.S.C. 154(b) by 170 days.

(21) Appl. No.: 15/122,893

(22) PCT Filed: May 8, 2015

(86) PCT No.: PCT/CN2015/078515
§ 371 (c)(1),
(2) Date: Aug. 31, 2016

(87) PCT Pub. No.: WO2015/169248
PCT Pub. Date: Nov. 12, 2015

(65) Prior Publication Data
US 2017/0067883 A1    Mar. 9, 2017

(30) Foreign Application Priority Data
May 8, 2014  (CN) .......................... 2014 1 0193851

(51) Int. Cl.
*G01N 33/53* (2006.01)
*G01N 35/04* (2006.01)
(Continued)

(52) U.S. Cl.
CPC ......... *G01N 33/5304* (2013.01); *G01N 21/76* (2013.01); *G01N 35/02* (2013.01);
(Continued)

(58) Field of Classification Search
CPC .... G01N 33/5304; G01N 21/76; G01N 35/02; G01N 35/04; G01N 2035/0401;
(Continued)

(56) References Cited

FOREIGN PATENT DOCUMENTS

CN    102183639 A    *    9/2011
CN    102183639 A        9/2011
(Continued)

OTHER PUBLICATIONS

European Patent Office Search Report for International Application No. No. PCT/CN2015/078515. dated Apr. 10, 2017.
(Continued)

*Primary Examiner* — Benjamin R Whatley
(74) *Attorney, Agent, or Firm* — Coats & Bennett, PLLC

(57) ABSTRACT

A reaction cuvette moving device and a fully automatic chemiluminescence immunoassay apparatus. The reaction cuvette moving device includes a transmission mechanism and a push mechanism, wherein the transmission mechanism comprises a baseplate and a first horizontal transmission mechanism provided on the baseplate. The push mechanism includes a support assembly, a second horizontal transmission mechanism provided on the support assembly, and a push rod connected to the second horizontal transmission mechanism.

10 Claims, 5 Drawing Sheets

(51) Int. Cl.
*G01N 21/76* (2006.01)
*G01N 35/02* (2006.01)

(52) U.S. Cl.
CPC ..... *G01N 35/04* (2013.01); *G01N 2035/0401* (2013.01); *G01N 2035/0465* (2013.01); *G01N 2035/0467* (2013.01); *G01N 2035/0482* (2013.01); *G01N 2035/0484* (2013.01)

(58) Field of Classification Search
CPC ... G01N 2035/0465; G01N 2035/0467; G01N 2035/0482; G01N 2035/0484
See application file for complete search history.

(56) References Cited

FOREIGN PATENT DOCUMENTS

| | | | |
|---|---|---|---|
| CN | 202735359 U | | 2/2013 |
| CN | 203519625 U | * | 4/2014 |
| CN | 203519625 U | | 4/2014 |
| CN | 203929792 U | | 11/2014 |
| GB | 2471298 A | | 12/2010 |
| JP | H10139152 A | | 5/1998 |
| WO | 2011036190 A2 | | 3/2011 |

OTHER PUBLICATIONS

International Search Report, International application No. PCT/CN2015/078515. dated Jul. 30, 2015. SIPO, Beijing, China.

* cited by examiner

REACTION CUVETTE LOADING DEVICE AND CHEMILUMINESCENCE IMMUNOASSAY APPARATUS

FIELD OF THE INVENTION

The invention relates to an external diagnostic apparatus, and more particularly relates to a reaction cuvette loading device and a chemiluminescence immunoassay apparatus using the reaction cuvette loading device.

BACKGROUND OF THE INVENTION

Biological chemiluminescence immunoassay is a non-radio immunoassay which is established by adopting a tracer ray machine as a signal tracer, based upon the theoretical basis of radio immunoassay; it processes advantages of a high sensitivity, a wider limiting scope, an easy operation and it is easy to realize an automatic operation. At present, a biochemical luminescence measurement apparatus based upon biological chemiluminescence immunoassay is a widely-used medical diagnostic apparatus. However, the commonly used biochemical luminescence measurement apparatus is expensive and has a huge volume, a greater power consumption, and it is difficult to popularize and promote the apparatus. Due to a high-speed development of the biomedical apparatus, a full automation of the biochemical luminescence measurement apparatus has certain conditions.

A full-automatic chemiluminescence immunoassay apparatus includes a reaction cuvette feeding system, a sampling system, an luminescence detecting system, a control system, and a software system. The reaction cuvette feeding system includes a reaction cuvette supplying and a reaction cuvette moving device, such existing devices mainly include two types: a first type by virtue of grasp, and a second type by directly pushing on an end of the reaction cuvette.

The conventional reaction cuvette loading device is mainly composed of a transmission mechanism and a pushing mechanism. A bottom plate of the transmission mechanism is provided with two raised synchronous belts parallel to each other, the synchronous belts transfer the reaction cuvette to the cuvette pushing position, and an automatic supplying of the reaction cuvette is achieved. The pushing mechanism pushes the reaction cuvette which is positioned on the cuvette pushing position to next working station by the push rod.

However, the conventional reaction cuvette loading device has the following disadvantages: when the push rod pushes the reaction cuvette, in order to bypass the reaction cuvette on the cuvette pushing position, the movement range of the push rod occupies a space of at least two cuvette positions, causing the overall volume of the product to be huge such that a greater space is occupied.

SUMMARY OF THE INVENTION

Accordingly, it is necessary to provide a reaction cuvette loading device which can reduce a volume of the product.

A reaction cuvette loading device includes: a transmission mechanism including a bottom plate, and a first horizontal transmission mechanism positioned on the bottom plate; and a pushing mechanism including: a bracket assembly; a second horizontal transmission mechanism positioned on the bracket assembly; a push rod connected to the second horizontal transmission mechanism and positioned on the bracket assembly; and a guiding control block including a starting end positioned on a terminal point of a reaction cuvette pushing stroke of the push rod; a terminating end positioned on a starting point of the cuvette pushing stroke of the push rod; and a return track positioned between the starting end and the terminating end and bypassing the cuvette pushing stroke, wherein a distance between the starting end and terminating end is greater than one cuvette position and less than two cuvette positions.

A chemiluminescence immunoassay apparatus includes the aforementioned reaction cuvette loading device.

In the embodiment of the invention, by virtue of providing a guiding control block, the push rod is controlled to return from a position above the reaction cuvette after the cuvette pushing action, thereby greatly reducing a movement range of the push rod, and shortening the movement time duration of the push rod, and the volume of product is reduced.

BRIEF DESCRIPTION OF THE DRAWINGS

In order to illustrate the technical solution of the invention or prior art more clearly, hereinafter, a brief introduction of accompanying drawings employed in the description of the embodiments or the prior art is provided. It is apparent that accompanying drawings described hereinafter merely are several embodiments of the invention. For one skilled in the art, other drawings can be obtained according to the accompanying drawings, without a creative work.

DETAILED DESCRIPTION OF THE EMBODIMENTS

The above and other objects, features and advantages of the present invention will become more apparent by describing in detail with reference to the accompanying drawings. It should be understood that the specific embodiments described herein are only used to explain the invention and is not intended to limit the invention.

Figure 1:
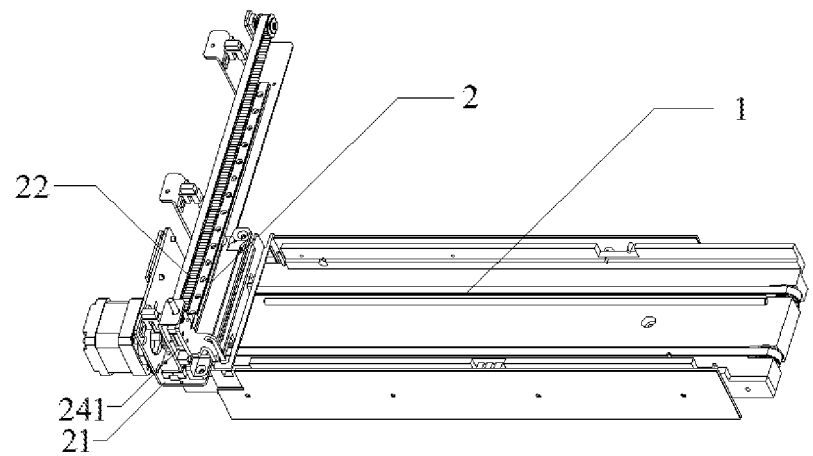
FIG. 1 is a perspective view of a reaction cuvette loading device according to a first embodiment.
Figure 2:
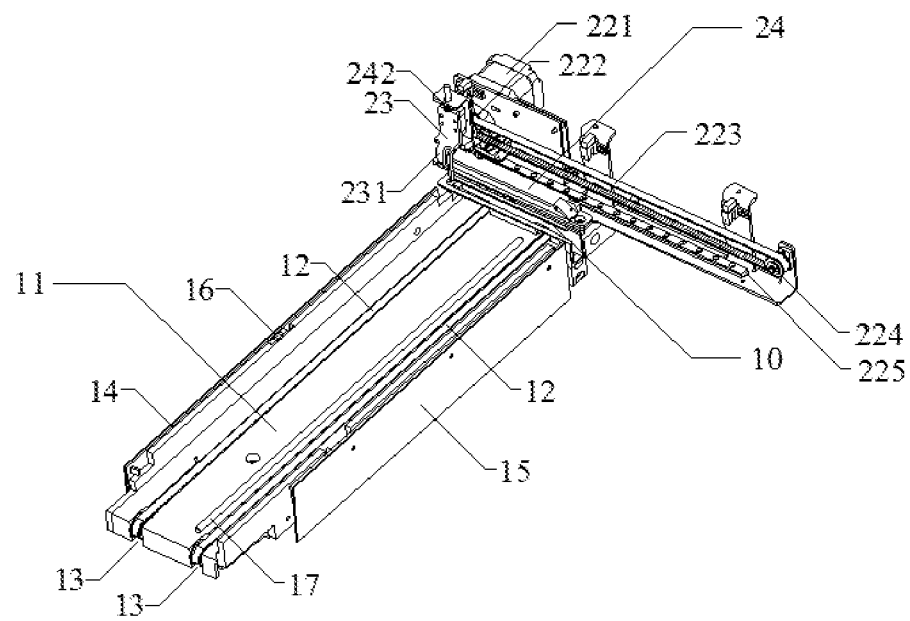
FIG. 2 is another perspective view of the reaction cuvette loading device according to the first embodiment.
Figure 3:
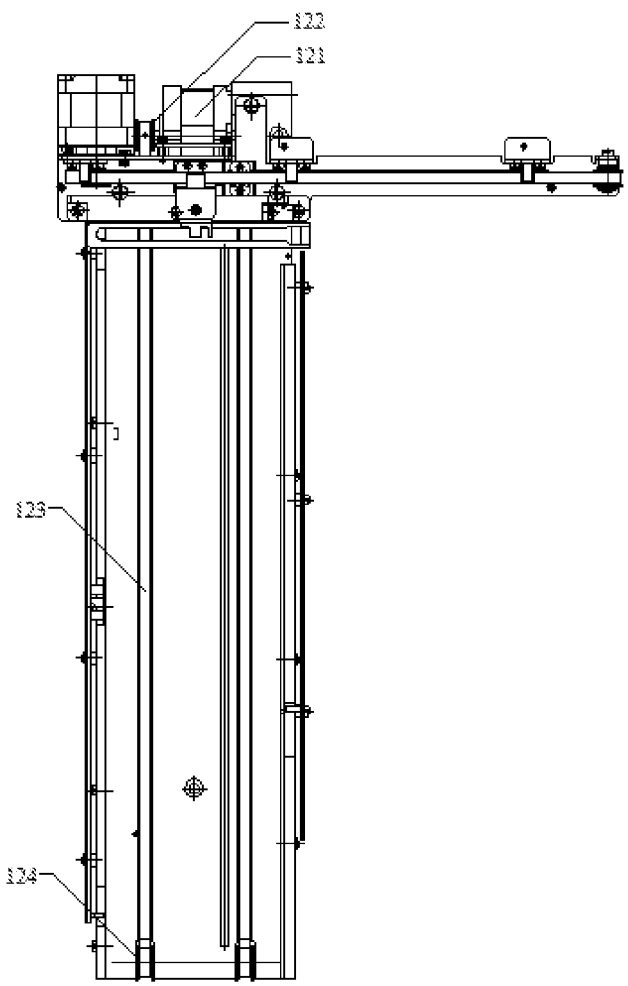
FIG. 3 is a front view of the reaction cuvette loading device according to the first embodiment.
Figure 4:
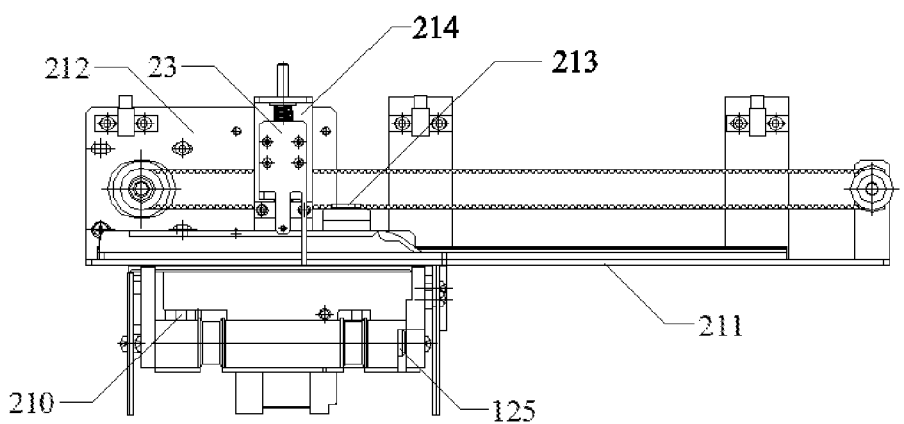
FIG. 4 is a top view of the reaction cuvette loading device according to the first embodiment.

A reaction cuvette loading device according to one embodiment is specifically illustrated with reference to FIG. 1 through FIG. 5. As shown in FIG. 1 and FIG. 2, the embodiment includes a transmission mechanism 1 and a pushing mechanism 2. The transmission mechanism 1 includes a bottom plate 11; a first horizontal transmission mechanism 12 positioned on the bottom plate 11; and a transmission groove 13 positioned on the bottom plate 11 and configured to receive the horizontal transmission mechanism 12. The push mechanism 2 includes a bracket assembly 21, a second horizontal transmission mechanism 22 positioned on the bracket assembly 21, a push rod 23 positioned on the bracket assembly 21 and connected to the second horizontal transmission mechanism 22; a vertical transmission mechanism 24 positioned on the bracket assembly 21 and connected to the push rod 23 and the second horizontal transmission mechanism 22; and a guiding control block 25 positioned along a cuvette pushing stroke of the push rod. The guiding control block 25 includes a starting end positioned on a terminal point of the cuvette pushing stroke of the push rod, a terminating end positioned on a start point of the cuvette pushing stroke of the push rod, and a return track positioned between the starting end and the terminating end and bypassing the cuvette pushing stroke.

Figure 5:
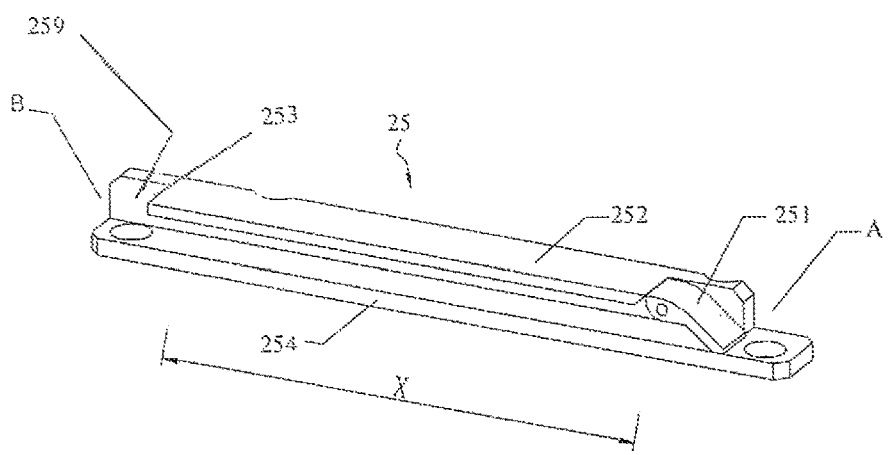
FIG. 5 is a perspective view of a guiding control block of the reaction cuvette loading device according to the first embodiment.
Figure 6:
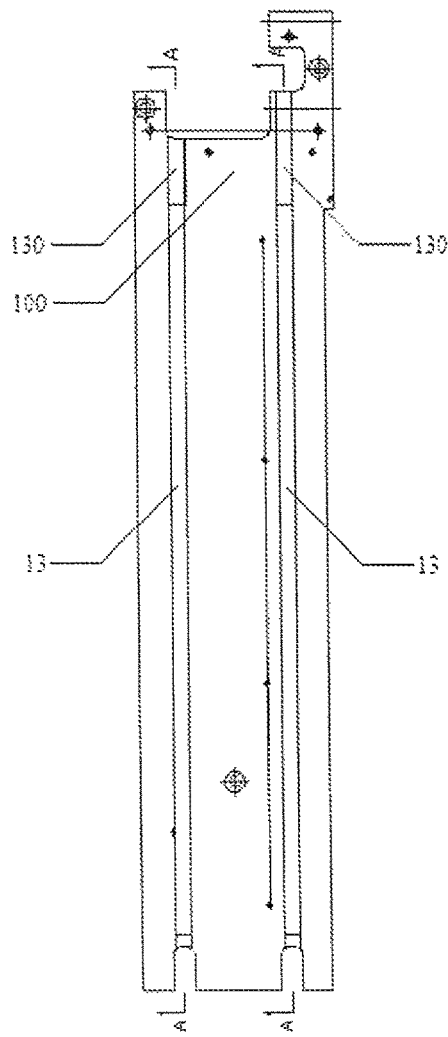
FIG. 6 is a front view of a bottom plate of a reaction cuvette loading device according to a second embodiment.
Figure 7:
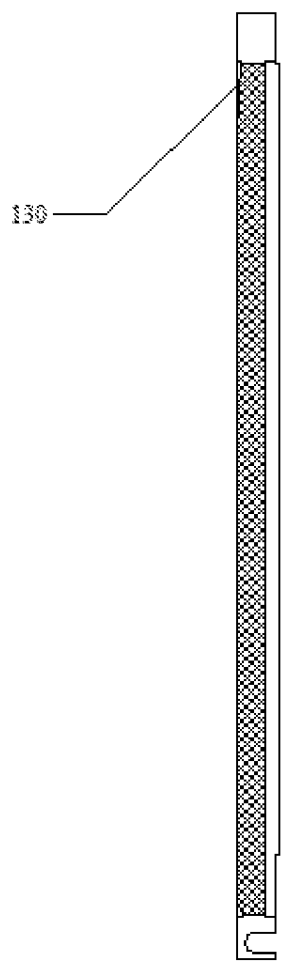
FIG. 7 is a cross-sectional view taken along lines A-A of FIG. 6.
Figure 8:
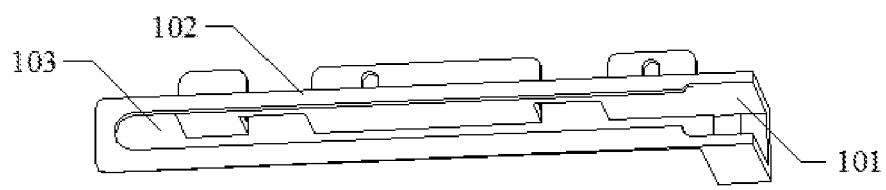
FIG. 8 is a perspective view of a reaction cuvette blocking plate of a reaction cuvette loading device according to a third embodiment.

In the embodiment as illustrated in FIG. 5, a distance between the starting end A and terminating end B is designed to be greater than one cuvette position X and less than two cuvette positions, and specifically, it is a little greater than one vessel position, an action space for a rising of the push rod 23 is reserved.

The guiding control block 25 of the embodiment is specifically illustrated in the following.

Specifically, the return track is configured to be a lifting track which includes an upward movement guiding surface 251 and a downward movement guiding surface 253.

Further, the lifting track further includes a horizontal movement guiding surface 2 positioned between the upward movement guiding surface 251 and the downward movement guiding surface 253.

Further, in order to reduce a resistance subjected in the return stroke by the push rod 23 and reduce the returning time, the upward movement guiding surface 251 can be designed as a smooth inclined surface, and the downward movement guiding surface 253 can be replaced by a landing opening which is positioned above the start point of the cuvette pushing stroke of the push rod.

Further, in order to reasonably fix the lifting track, the guiding control block 25 further includes a guiding base 254. The guiding base 254 includes an assembly bottom plate and an assembly side plate extending upwardly from a rear side of the assembly bottom plate. The horizontal movement guiding surface 252 is parallel to the assembly bottom plate and assembled to a middle position of the assembly side plate. The landing opening 259 is joined to a terminating end of the horizontal movement guiding surface 252, and a top end of the upward movement guiding surface 251 is smoothly connected to a starting end of the horizontal movement guiding surface 252. A bottom end is connected to the assembly bottom plate.

Further, in order to better guide the return stroke of the push rod 23 by the guiding control block 25, the push rod 23 is further provided with a guiding pin 231 engaging the guiding control block 25. The guiding pin 231 slidably extends into the guiding control block 25.

It should be noted that, in addition to the structure of the lifting structure of above mode, the lifting structure can be designed to be other structures. For example, it can be designed that the upward movement guiding surface is directly connected to the downward movement guiding surface to form an arc-shaped or an arch-shaped smooth surface. The push rod moves upward and downward along the smooth surface, and an object of bypassing the cuvette pushing stroke when moving from the terminal point to the start point can also be achieved. Other return stroke structures designed by a common sense which is readily envisaged and aiming at the target should also be included in the scope of the invention.

The first horizontal transmission mechanism 12 according to the embodiment is specifically illustrated in the following.

Specifically, the first horizontal transmission mechanism 12 can specifically include: a transmission motor 121 fixed to a tail end of the bottom plate 11; two first synchronous belt driving wheels 122 axially connected to opposite ends of the transmission motor 121; two first synchronous driven pulleys 124 positioned on a front end of the two transmission grooves 13 respectively, and connected to the two first synchronous belt driving wheels 122 via two first synchronous belts 123; a rotation shaft 125 axially connected to the two first synchronous driven pulleys 124; and a first horizontal linear guide 17 positioned on the bottom plate 11 and parallel to the first transmission groove 13. In the embodiment, under the occasion when the reaction cuvette can be stability transferred along a determined direction, the first horizontal linear guide 17 is not required.

The bracket assembly 21 according to the embodiment is specifically illustrated in the following.

Specifically, the bracket assembly 21 can specifically include: a supporting post 210 extending upwardly from the tail end of the bottom plate 11; a horizontal assembly surface 211 positioned above the supporting post 210; a vertical assembly surface 212 extending upward from a rear side of the horizontal assembly surface 211; and a connecting block 214 positioned on a front side of the vertical assembly surface 212 and connected to the second horizontal transmission mechanism 22 via a connecting block buckle 213, with the connecting block 214 configured to fix the push rod 23. The second horizontal transmission mechanism 22 according to the embodiment is specifically illustrated in the following.

Specifically, the second horizontal transmission mechanism 22 can specifically include: a pushing motor 221 fixed to a rear side of an end of the vertical assembly surface 212; a second synchronous belt driving wheel 222 axially connected to the pushing motor 221; a second synchronous driven pulley 224 connected to the second synchronous belt driving wheel 222 via a second synchronous belt 223; a second horizontal linear guide 225 positioned on the vertical assembly surface 211 and parallel to the second synchronous belt 223. The vertical transmission mechanism 24 according to the embodiment is specifically illustrated in the following.

Specifically, the vertical transmission mechanism 24 can specifically include: a vertical linear guide 241 vertically positioned on the bracket assembly and rigidly connected to the push rod and the second horizontal transmission mechanism; and a resilient connector 242 vertically positioned between the push rod and the bracket assembly.

Further, both the push rod 23 and the vertical linear guide 241 are positioned on the connecting block 241 of the bracket assembly 21, the resilient connector 242 is positioned between a top end of the connecting block 214 and a top end of the push rod 23, and the connecting block 214 is connected to the second horizontal linear guide 225 via the connecting block buckle 213.

The working principle according to the embodiment is specifically illustrated in the following.

When working, the transmission motor 121 rotates to drive the first synchronous belt 123 in the transmission groove 13 to move forward, and transfers the reaction cuvette positioned on the bottom plate 11 to the cuvette pushing position 100. The reaction cuvette is blocked by a front blocking surface 101 of a reaction cuvette blocking plate 10 to stop. The reaction cuvette is positioned on the cuvette pushing position 100 to wait for a push by the push rod 23 to the next working station.

The pushing motor 221 rotates to drive the horizontal linear guide 225 to move horizontally via the second synchronous belt 223, and driving the push rod 23 to push the reaction cuvette to the next working station; in the return stroke, the guiding control block 25 engages with the guiding pin 231 to cause the push rod 23 to perform a lifting motion at the same time moving horizontally, thereby bypassing the cuvette pushing stroke. When a highest portion of the upward movement guiding surface 251 is reached, the push rod 23 stops the lifting movement, at the time, the push rod 23 is higher than a top surface of the reaction cuvette, under the guiding function the horizontal movement guiding surface 252, the push rod 23 merely performs a horizontal movement and moves to a terminal end of the reaction cuvette from a position above the reaction cuvette, thereby bypassing the reaction cuvette on the cuvette pushing position 100. At the terminal end position of the reaction cuvette, the guiding pin 231 departs a guiding function of the guiding control block 25 from the landing opening 259, the push rod 23 moves down and pushes the reaction cuvette, and a new round of the cuvette pushing motion is initiated, and an object of loading the reaction cuvette is achieved.

In the embodiment, by virtue of providing a guiding control block 25 between the start point and the terminal point of the cuvette pushing stroke of the push rod, the push rod 2 is controlled to return along a return track and bypasses the cuvette pushing stroke (i.e. the position of the reaction cuvette), thereby greatly reducing a movement range of the push rod 2, and shortening the movement time duration of the push rod 23, not only the volume of the product is reduced, but also the working efficiency is improved.

The second embodiment according to the invention is specifically illustrated with reference to FIG. 1 through FIG. 4, and FIG. 6 and FIG. 7 in the following. The core of the embodiment is that, on basis of above described first embodiment, the structure of the bottom plate is improved. The detail is that two transmission grooves 13 which are parallel to each other are provided on the bottom plate 11 and configured to receive the first horizontal transmission mechanism 12. Each transmission groove 13 is designed to be inclined downwardly at a position corresponding to the cuvette pushing position on the tail end of the bottom plate 11, i.e. inclined toward a direction away from first horizontal transmission mechanism 12, to form a passage of inclined surface structure 130. An inclined angle of the inclined surface structure 130 relative to the first horizontal transmission mechanism 12 is designed to be 2-5 degrees.

Further, a left side plate 14 and a right side plate 15 are formed by extending from a left side and a right side of the bottom plate 11. The left side plate 14 and/or the right side plate 15 are provided with a reaction cuvette sensor 16 which is electrically connected to a control circuit, the reaction cuvette sensor 16 can adopt three optical coupling devices.

The working principle according to the embodiment is specifically illustrated in the following.

When working, the transmission motor 121 rotates to drive the first synchronous belt 123 to move forward, and transfers the reaction cuvette which is positioned on the bottom plate 11 to the cuvette pushing position 100. The reaction cuvette is blocked by the front blocking surface 101 of the reaction cuvette blocking plate 10 to stop, the reaction cuvette is positioned on the cuvette pushing position 100 to wait for being pushed by the push rod 23 to next working station. Because the position of transmission groove 13 corresponding to the cuvette pushing position 100 has an inclined structure, causing a position of the first synchronous belt 123 on the inclined structure is lower than the surface of the bottom plate 11, thereby eliminating a scrap and a crash between the reaction cuvette and the first synchronous belt 123 when the reaction cuvette moves laterally, and a dump problem of the reaction cuvette caused thereby is avoided.

The pushing motor 221 rotates to drive the horizontal linear guide 225 to move horizontally via the second synchronous belt 223, and drive the push rod 23 to push the reaction cuvette to the next working station; in the return stroke, the guiding control block 25 engages with the guiding pin 231 to cause the push rod 23 to perform a lifting motion at the time of moving horizontally. When the highest portion of the upward movement guiding surface 251 is reached, the push rod 23 stops the lifting movement, at the time, the push rod 23 is higher than a top surface of the reaction cuvette. Under the guiding function of the horizontal movement guiding surface 252, the push rod 23 merely performs a horizontal movement and moves to a terminal end of the reaction cuvette from a position above the reaction cuvette, thereby bypassing the reaction cuvette on the cuvette pushing position 100. At the terminal end position of the reaction cuvette, the guiding pin 231 departs from the guiding function of the guiding control block 25 on the landing opening 259, the push rod 23 moves down and pushes the reaction cuvette, and a new round of cuvette pushing motion is initiated, and an object of loading the reaction cuvette is achieved.

In the embodiment, a position of the first synchronous belt is lower than the surface of the bottom plate by virtue of designing the transmission groove on the position corresponding to the cuvette pushing position as an inclined structure, thereby eliminating a scrap and a crash between the reaction cuvette and the synchronous belt when the reaction cuvette moves laterally, eliminating a dump problem of the reaction cuvette caused thereby, and a reliability of the product is improved The third embodiment according to the invention is specifically illustrated with reference to FIG. 1 through FIG. 4, and FIG. 8 in the following. The core of the embodiment is that, on basis of above described first embodiment, the structure of the reaction cuvette blocking plate 10 is improved. The detail is that, the reaction cuvette blocking plate 10 includes a front blocking surface 101, and an upper blocking surface 102 extending forward from a top end of the front blocking surface 101.

Specifically, the upper blocking surface 102 defines a push rod groove 103 for the push rod 23 to extend through, a left end of the push rod groove 103 is closed, a right end of the push rod groove 103 is opened.

The working principle according to the embodiment is specifically illustrated in the following.

When working, the transmission motor 121 rotates to drive the first synchronous belt 123 to move forward, and transfers the reaction cuvette on the bottom plate 11 to the cuvette pushing position 100, the reaction cuvette is blocked by a front blocking surface 101 of a reaction cuvette blocking plate 10 to stop, the reaction cuvette is positioned on the cuvette pushing position 100 to wait for being pushed by the push rod 23 to next working station, at the same time, the upper blocking surface 102 of the reaction cuvette blocking plate 10 limits an upward movement of the reaction cuvette, a runout generated when the reaction cuvette moves is avoided.

The pushing motor 221 rotates to drive the horizontal linear guide 225 to move horizontally via the second synchronous belt 223, and driving the push rod 23 to push the reaction cuvette to the next working station; in the return stroke, the guiding control block 25 engages the guiding pin 231 to cause the push rod 23 to perform a lifting motion at the same time of moving horizontally. When a highest portion of the upward movement guiding surface 251 is reached, the push rod 23 stops the lifting movement, at the time, the push rod 23 is higher than a top surface of the reaction cuvette. Under the guiding function of the horizontal movement guiding surface 252, the push rod 23 merely performs a horizontal movement and moves to a terminal end of the reaction cuvette from a position above the reaction cuvette, thereby bypassing the reaction cuvette on the cuvette pushing position 100. At the terminal end of the reaction cuvette, the guiding pin 231 departs from the guiding function of the guiding control block 25 on the landing opening 259, the push rod 23 moves down and pushes the reaction cuvette, and a new round of cuvette pushing motion is initiated, and an object of loading the reaction cuvette is achieved.

In the embodiment, by virtue of additionally providing a top blocking surface on the top end of the reaction cuvette blocking plate to guide and control a movement direction of the reaction cuvette, thereby effectively avoiding a runout phenomenon caused by the reaction cuvette movement, and a malfunction caused by the reaction cuvette stuck problem which is generated thereby is eliminated correspondingly, and a reliability of the product is improved The fourth embodiment according to the invention is specifically illustrated with reference to FIG. 1 through FIG. 8 in the following. The core of the embodiment is that, on basis of above described third embodiment, the structure of the reaction cuvette blocking plate 10 is improved. The improvement thereof is same as the improvement to the reaction cuvette blocking plate in the foregoing fourth embodiment, and is not specifically described herein.

The working principle according to the embodiment is specifically illustrated in the following.

When working, the transmission motor 121 rotates to drive the first synchronous belt 123 to move forward, and transfers the reaction cuvette positioned on the bottom plate 11 to the cuvette pushing position 100, the reaction cuvette is blocked by the front blocking surface 101 of the reaction cuvette blocking plate 10 to stop, the reaction cuvette is positioned on the cuvette pushing position 100 to wait for being pushed by the push rod 23 to next working station. Because a position of the transmission groove 13 corresponding to the cuvette pushing position 100 has an inclined structure, causing the position of the first synchronous belt 123 on the inclined structure is lower than the surface of the bottom plate 11, thereby eliminating a scrap and a crash between the reaction cuvette and the first synchronous belt 123 when the reaction cuvette moves laterally, and a dump problem of the reaction cuvette caused thereby is avoided, at the same time, the upper blocking surface 102 of the reaction cuvette blocking plate 10 limits an upward movement of the reaction cuvette, a runout generated when the reaction cuvette moves is avoided.

The pushing motor 221 rotates to drive the horizontal linear guide 225 to move horizontally via the second synchronous belt 223, and drives the push rod 23 to push the reaction cuvette to the next working station; in the return stroke, the guiding control block 25 engages the guiding pin 231 to cause the push rod 23 perform a lifting motion at the time of moving horizontally. When a highest portion of the upward movement guiding surface 251 is reached, the push rod 23 stops the lifting movement, at the time, the push rod 23 is higher than a top surface of the reaction cuvette, under the guiding function the horizontal movement guiding surface 252, the push rod 23 merely performs a horizontal movement and moves to a terminal end of the reaction cuvette from a position above the reaction cuvette, thereby bypassing the reaction cuvette on the cuvette pushing position 100. At the terminal end of the reaction cuvette, the guiding pin 231 departs from the guiding function of the guiding control block 25 on the landing opening 259, the push rod 23 moves down and pushes the reaction cuvette, and a new round of the cuvette pushing motion is initiated, and an object of loading the reaction cuvette is achieved Compared to the prior art, the embodiment possesses at least the following advantages:

The guiding control block is provided, the push rod is controlled to return along the return track and bypasses the position of the reaction cuvette, thereby greatly reducing a movement range of the push rod, and shortening the movement time duration of the push rod, not only the volume of the product is reduced, but also the working efficient is improved.

The transmission groove on the position corresponding to the cuvette pushing position has an inclined structure, causing the first synchronous belt on the position of the transmission groove to be lower than the surface of the bottom plate, thereby eliminating a scrap and a crash between the reaction cuvette and the first synchronous belt when the reaction cuvette moves laterally, and a dump problem of the reaction cuvette caused thereby is avoided.

A top blocking surface is additionally provided on the top end of the reaction cuvette blocking plate to guide and control a movement direction of the reaction cuvette, thereby effectively avoiding a runout phenomenon caused by the reaction cuvette movement, and a malfunction caused by the reaction cuvette stuck problem which is generated thereby is eliminated correspondingly, and a reliability of the product is improved.

Figure 9:
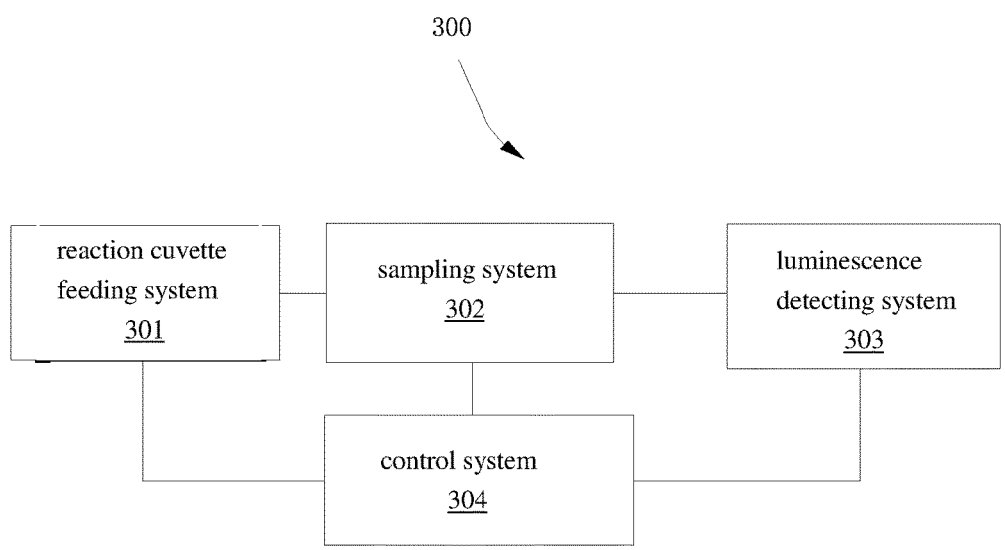
FIG. 9 is a block diagram of a chemiluminesence immunoassay apparatus according to an embodiment.

Referring to FIG. 9, a chemiluminescence immunoassay apparatus 300 disclosed in an embodiment includes a reaction cuvette feeding system 301, a sampling system 302, a luminescence detecting system 303, and a control system 304. The reaction cuvette feeding system 301 can adopt any one of the reaction cuvette loading device described in above embodiments, something in common is not described herein for simple.

The specific embodiment of the invention is fully disclosed with reference to the foregoing description. It should be noted that variations and improvements will become apparent to those skilled in the art to which the present invention pertains without departing from its spirit and scope. Accordingly, the scope of the present invention is not merely defined by the foregoing specific embodiment.

What is claimed is:
1. A device to move reaction cuvettes, comprising:
a transmission mechanism to move the reaction cuvettes in a first direction, the transmission mechanism comprising a bottom plate and a first horizontal transmission mechanism positioned on the bottom plate, the transmission mechanism including a cuvette pushing position sized to position one of the reaction cuvettes; and a pushing mechanism positioned at one end of the transmission mechanism and configured to move the reaction cuvettes in a second direction that is transverse to the first direction, the pushing mechanism comprising:
  a bracket assembly;
  a second horizontal transmission mechanism positioned on the bracket assembly;
  a push rod positioned on the bracket assembly and connected to the second horizontal transmission mechanism, the push rod moving across the one end of the transmission mechanism in a pushing stroke to push the reaction cuvettes and a return stroke, the push rod further comprising a guiding pin;
  a vertical transmission mechanism that is positioned on the bracket assembly and connected to the push rod and the second horizontal transmission mechanism;
  the vertical transmission mechanism comprising a vertical linear guide vertically positioned on the bracket assembly and connected to the push rod and the second horizontal transmission mechanism and a resilient connector vertically positioned between the push rod and the bracket assembly; and
  a guiding control block, which engages the guiding pin, comprising: a starting end positioned on a terminal point of a cuvette pushing stroke of the push rod; a terminating end positioned on a start point of the cuvette pushing stroke of the push rod; and a return track positioned between the starting end and the terminating end, the return track comprising an inclined upward movement guiding surface, a downward movement guiding surface, and an intermediate horizontal movement guiding surface between the upward and downward movement guiding surfaces, the guiding pin of the push rod slidably extends into the guiding control block and along the guiding surfaces, the return track configured to lift the push rod upward such that the push rod is lifted higher than a top surface of the reaction cuvettes while moving horizontally and bypassing the cuvette pushing stroke, wherein a distance between the starting end and terminating end is greater than one cuvette position and less than two cuvette positions;
  wherein the transmission mechanism further comprises a reaction cuvette blocking plate positioned beneath a front of the guiding control block, with an upper blocking surface to limit an upward movement of the reaction cuvette, the upper blocking surface defines a push rod groove for the push rod to extend through, a left end of the push rod groove is closed, and a right end of the push rod groove is opened.

2. The device according to claim 1, wherein the upward movement guiding surface is a smooth inclined surface.

3. The device according to claim 2, wherein the guiding control block further comprises a guiding base and a landing opening, the guiding base comprises an assembly bottom plate and an assembly side plate extending upwardly from a rear side of the assembly bottom plate, the horizontal movement guiding surface is parallel to the assembly plate and assembled to a middle position of the assembly side plate, the landing opening is joined to a terminating end of the horizontal movement guiding surface, and a top end of the upward movement guiding surface is connected to the horizontal movement guiding surface, a bottom end of the upward movement guiding surface is connected to the assembly bottom plate.

4. The device according to claim 1, wherein the bottom plate defines two transmission grooves which are parallel to each other and configured to receive the first horizontal transmission mechanism, and each transmission groove is inclined downwardly at a position corresponding to the cuvette pushing position.

5. The device according to claim 4, wherein the inclined downward angle relative to the first horizontal transmission mechanism ranges from 2 to 5 degrees.

6. A chemiluminescence immunoassay apparatus, comprising:
  a sampling system;
  a luminescence detecting system;
  a control system;
  a reaction cuvette feeding system, comprising:
    a transmission mechanism to move a reaction cuvette in a first direction, the transmission mechanism comprising a bottom plate and a first horizontal transmission mechanism positioned on the bottom plate, the transmission mechanism including a cuvette pushing position sized to position the reaction cuvette; and
    a pushing mechanism positioned at one end of the transmission mechanism and configured to move the reaction cuvette in a second direction that is transverse to the first direction, the pushing mechanism comprising:
    a bracket assembly;
    a second horizontal transmission mechanism positioned on the bracket assembly;
    a push rod positioned on the bracket assembly and connected to the second horizontal transmission mechanism, the push rod moving across the one end of the transmission mechanism in a pushing stroke to push the reaction cuvette and a return stroke, the push rod further comprising a guiding pin;
    a vertical transmission mechanism that is positioned on the bracket assembly and connected to the push rod and the second horizontal transmission mechanism, the vertical transmission mechanism comprising a vertical linear guide vertically positioned on the bracket assembly and connected to the push rod and the second horizontal transmission mechanism and a resilient connector vertically positioned between the push rod and the bracket assembly; and
    a guiding control block that receives and engages the guiding pin of the push rod, the guiding control block comprising:
      a starting end positioned on a terminal point of a cuvette pushing stroke of the push rod;
      a terminating end positioned on a start point of the cuvette pushing stroke of the push rod; and
      a return track positioned between the starting end and the terminating end, the return track comprising an inclined upward movement guiding surface, a downward movement guiding surface, and an intermediate horizontal movement guiding surface between the upward and downward movement guiding surfaces, the guiding pin of the push rod slidably extends into the guiding control block and along the guiding surfaces, the return track configured to lift the push rod upward such that the push rod is lifted higher than a top surface of the reaction cuvette while moving horizontally and bypassing the cuvette pushing stroke,
    wherein a distance between the starting end and terminating end is greater than one cuvette position and less than two cuvette positions;

wherein the transmission mechanism further comprises a reaction cuvette blocking plate positioned beneath a front of the guiding control block, with an upper blocking surface to limit an upward movement of the reaction cuvette, the upper blocking surface defines a push rod groove for the push rod to extend through, a left end of the push rod groove is closed, and a right end of the push rod groove is opened.

7. The chemiluminescence immunoassay apparatus according to claim 6, wherein the upward movement guiding surface is a smooth inclined surface.

8. The chemiluminescence immunoassay apparatus according to claim 7, wherein the guiding control block further comprises a guiding base and a landing opening, the guiding base comprises an assembly bottom plate and an assembly side plate extending upwardly from a rear side of the assembly bottom plate, the horizontal movement guiding surface is parallel to the assembly plate and assembled to a middle position of the assembly side plate, the landing opening is joined to a terminating end of the horizontal movement guiding surface, and a top end of the upward movement guiding surface is connected to the horizontal movement guiding surface, a bottom end of the upward movement guiding surface is connected to the assembly bottom plate.

9. The chemiluminescence immunoassay apparatus according to claim 6, wherein the bottom plate defines two transmission grooves which are parallel to each other and configured to receive the first horizontal transmission mechanism, and each transmission groove is inclined downwardly at a position corresponding to the cuvette pushing position.

10. The chemiluminescence immunoassay apparatus according to claim 9, wherein the inclined downward angle relative to the first horizontal transmission mechanism ranges from 2 to 5 degrees.

* * * * *